United States Patent [19]

Howson et al.

[11] Patent Number: 4,804,054

[45] Date of Patent: Feb. 14, 1989

[54] DEVICE AND METHOD FOR PRECISE SUBCUTANEOUS PLACEMENT OF A MEDICAL INSTRUMENT

[75] Inventors: David C. Howson, Denver; J. Donald Pauley, Estes Park; Gary T. Carroll, Boulder, all of Colo.

[73] Assignee: Intelligent Medicine, Inc., Englewood, Colo.

[21] Appl. No.: 55,986

[22] Filed: Jun. 1, 1987

[51] Int. Cl.[4] .............................................. A61B 19/00
[52] U.S. Cl. ...................................... 128/898; 604/48; 128/897
[58] Field of Search ................. 128/303.18, 303.19, 128/1.3, 1.4, 1.5, 639, 1 R, DIG. 12; 604/158, 160, 174, 891, 152, 67, 48

[56] References Cited

U.S. PATENT DOCUMENTS

| | | | |
|---|---|---|---|
| 3,350,660 | 10/1967 | Engdahl et al. | 331/65 |
| 3,744,044 | 7/1973 | Vosteen | 340/507 |
| 3,889,249 | 6/1975 | Bennett, Jr. et al. | 340/568 |
| 3,935,542 | 1/1976 | Buck | 331/65 |
| 4,004,234 | 1/1977 | Juvinall | 328/5 |
| 4,160,454 | 7/1979 | Foux | 604/93 |
| 4,222,374 | 9/1980 | Sampson et al. | 128/1 R |
| 4,299,230 | 11/1981 | Kubota | 128/630 |
| 4,407,294 | 10/1983 | Vilkomerson | 128/660 |
| 4,431,006 | 2/1984 | Trimmer et al. | 128/660 |
| 4,502,042 | 2/1985 | Wuhrl et al. | 340/568 |
| 4,535,773 | 8/1985 | Yoon | 604/51 |
| 4,539,003 | 9/1985 | Tucker | 604/93 |
| 4,543,088 | 9/1985 | Bootman et al. | 604/93 |
| 4,573,994 | 3/1986 | Fischell et al. | 604/891 |
| 4,583,977 | 4/1986 | Shishov et al. | 604/174 |
| 4,697,595 | 10/1987 | Breyer et al. | 128/660 |

Primary Examiner—Francis J. Jaworski
Assistant Examiner—George Manuel
Attorney, Agent, or Firm—Robert E. Harris

[57] ABSTRACT

A device and method for precise placement of a medical instrument for fluid delivery at, or withdrawal of fluid from, a predetermined location in a body is disclosed. A sensor, such as a proximity detector or electrically conductible circuitry, is implanted into the body adjacent to a predetermined location, which location preferably has an implanted reservoir thereat, for sensing the position of a medical instrument having an open end portion inserted into the reservoir to enable delivery of medicament into the reservoir or, in the alternative, to remove fluid from the reservoir. A signal indicative at least of a sensed desired positioning of the instrument is generated and used to assure that the instrument has been properly positioned, with additional circuitry also being provided to enable location of the implanted reservoir for positioning of the instrument prior to insertion into the body.

30 Claims, 7 Drawing Sheets

U.S. Patent  Feb. 14, 1989  Sheet 1 of 7  4,804,054
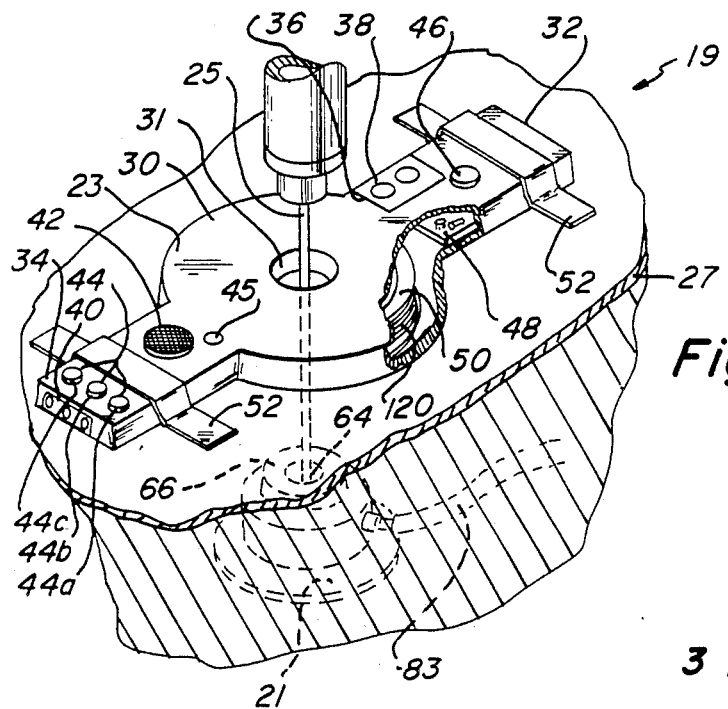
Fig_1
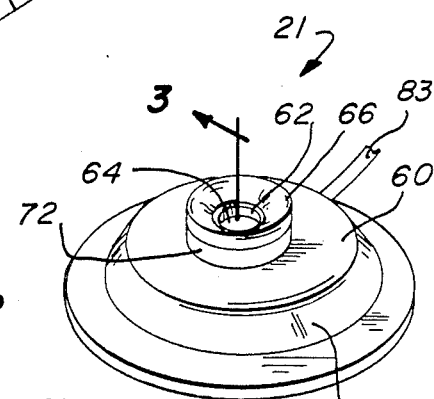
Fig_2
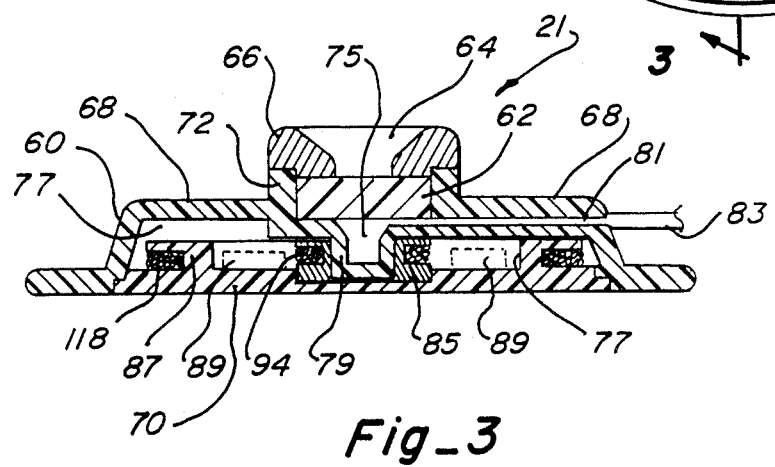
Fig_3

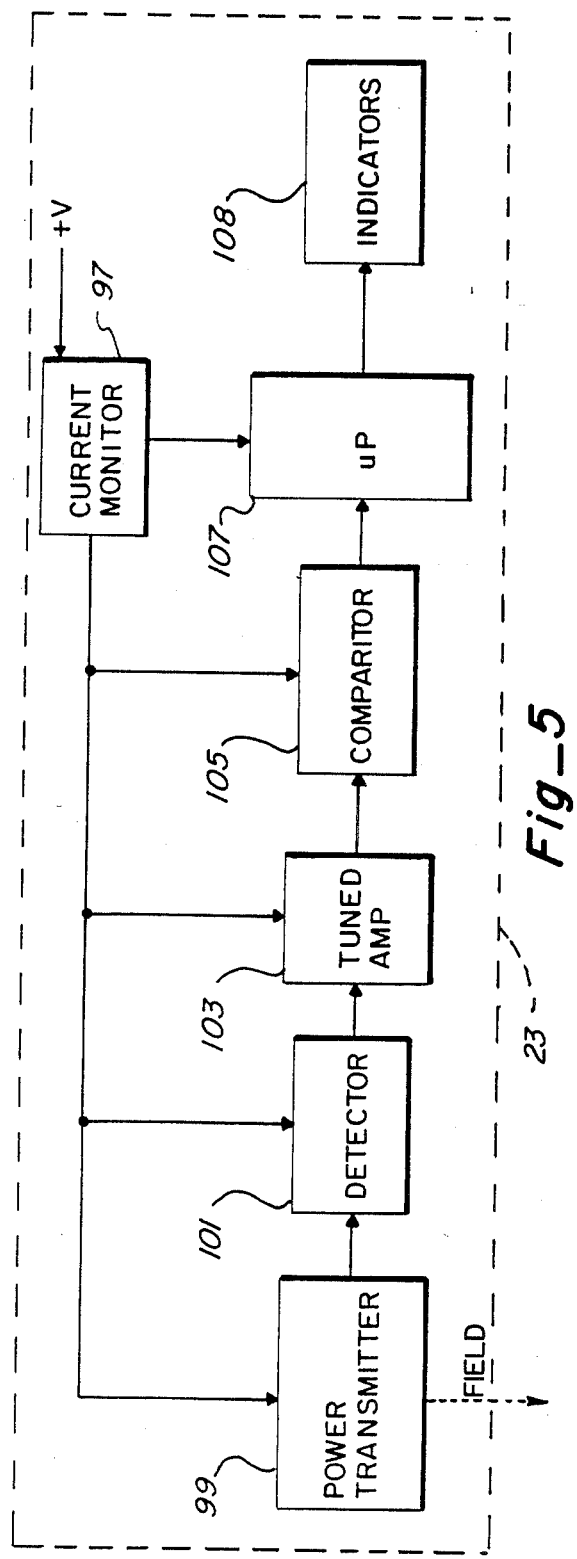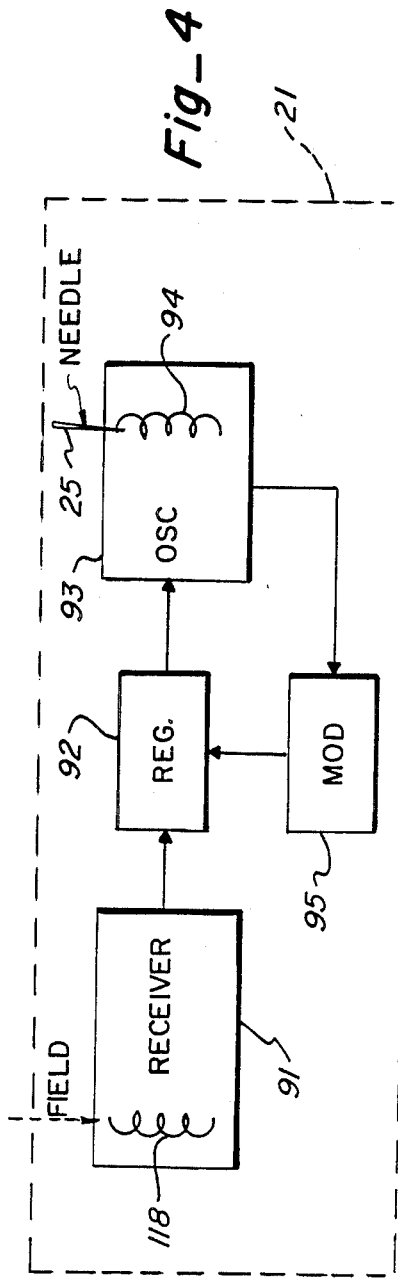

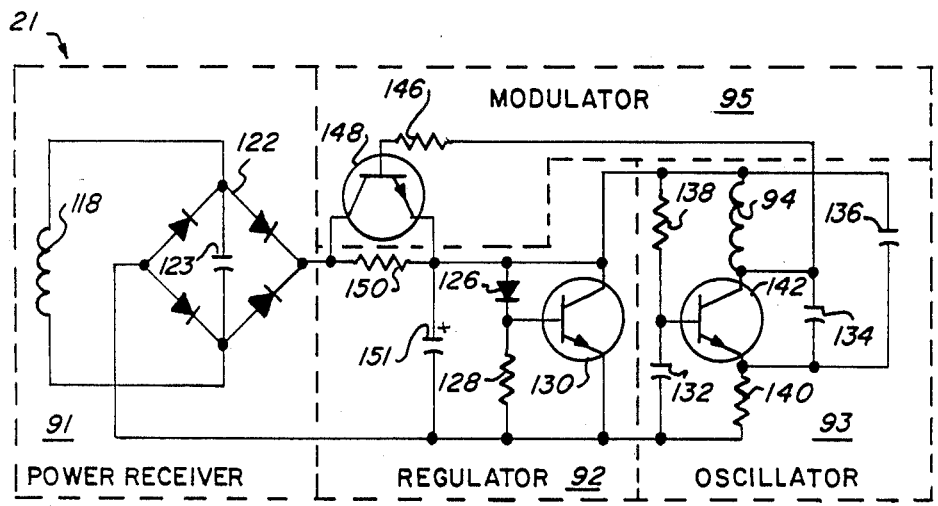
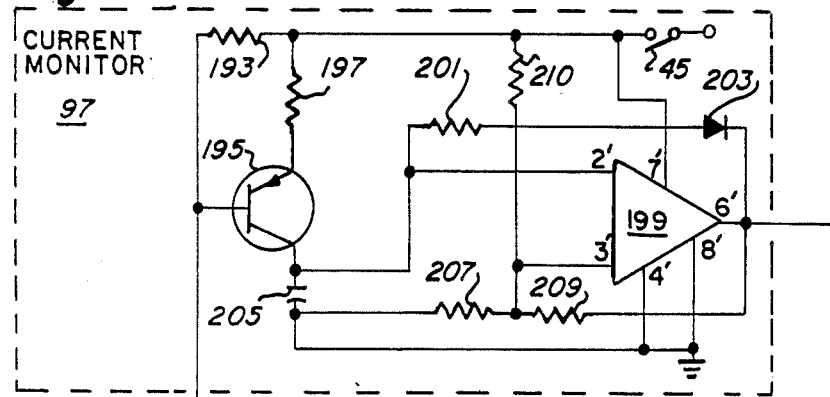
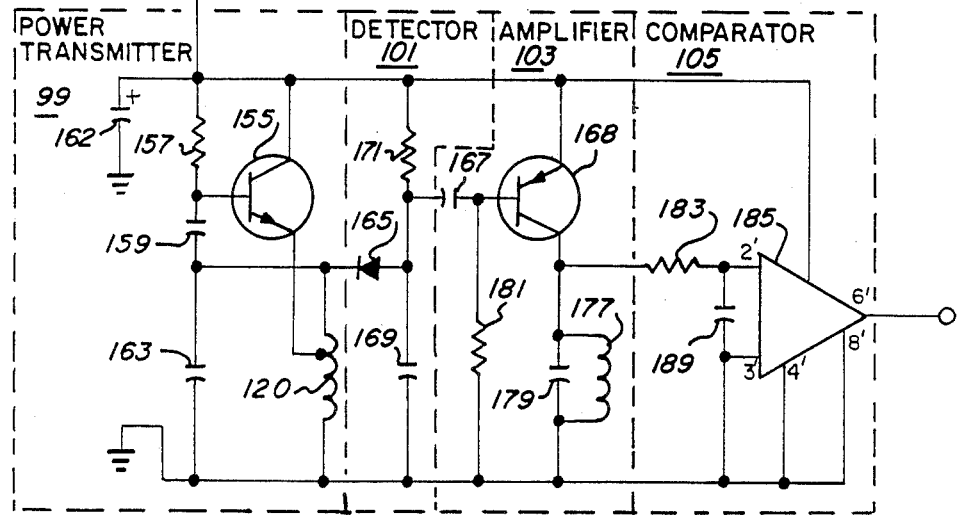
Fig_6
Fig_7

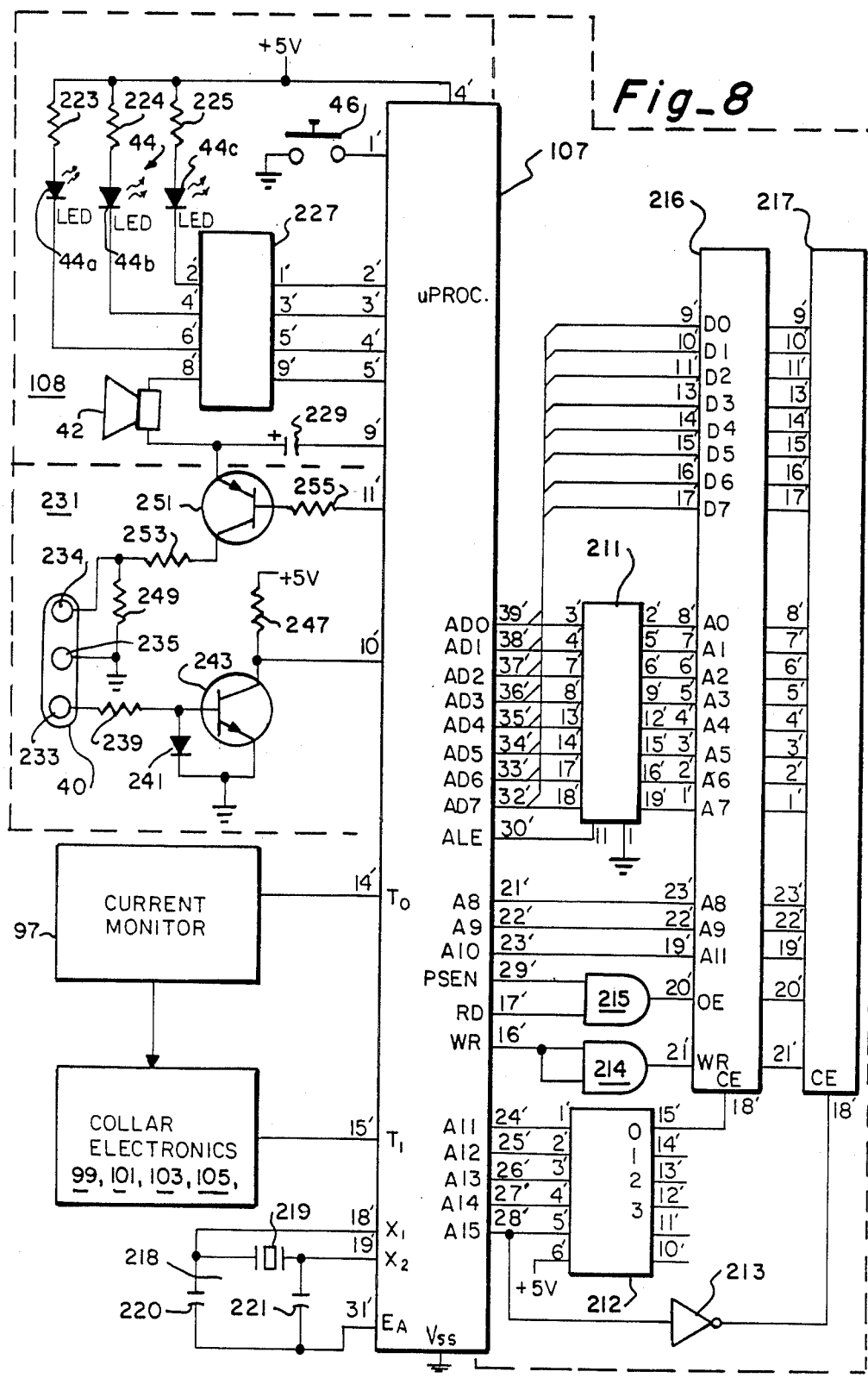
Fig_8

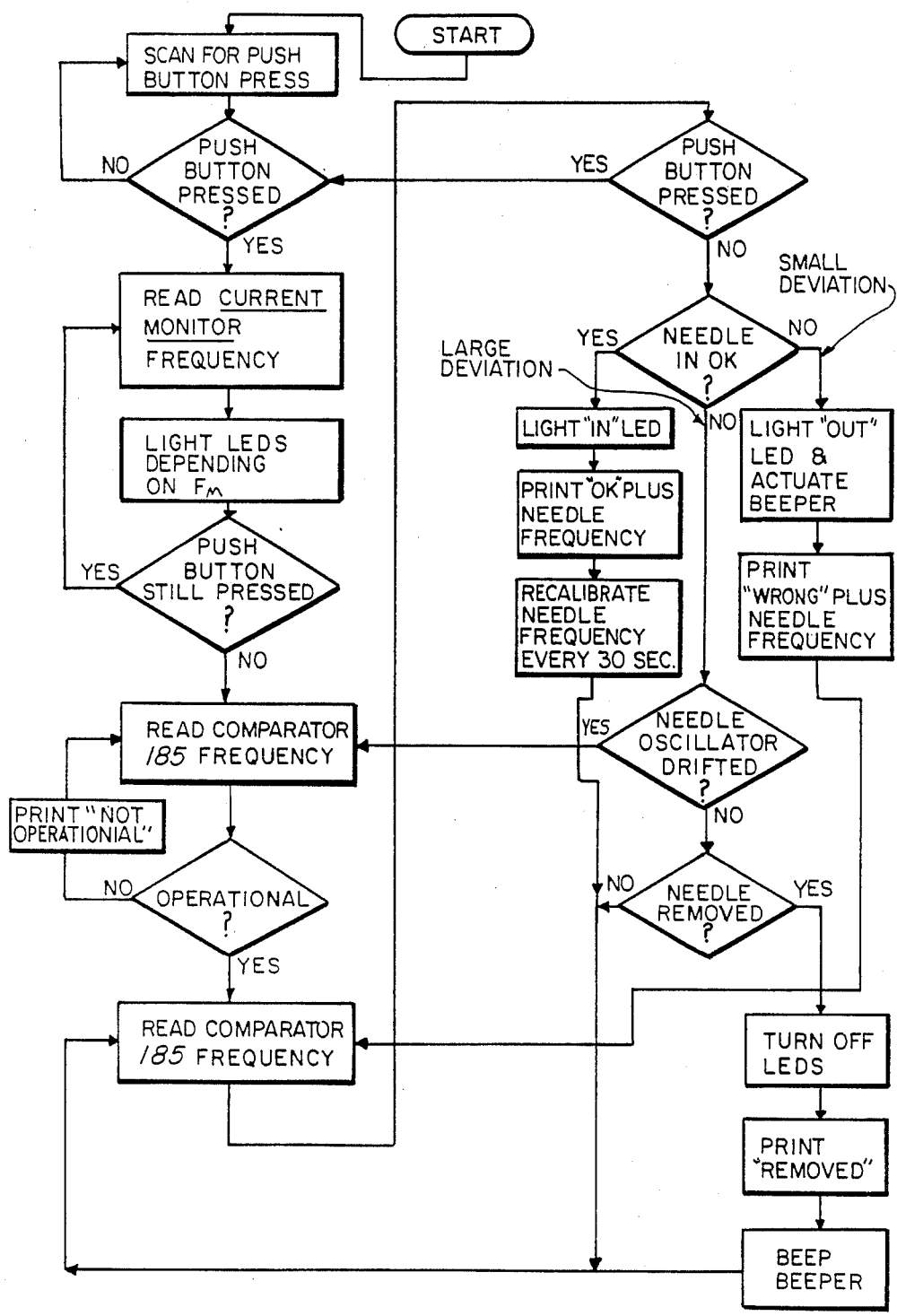
Fig_9

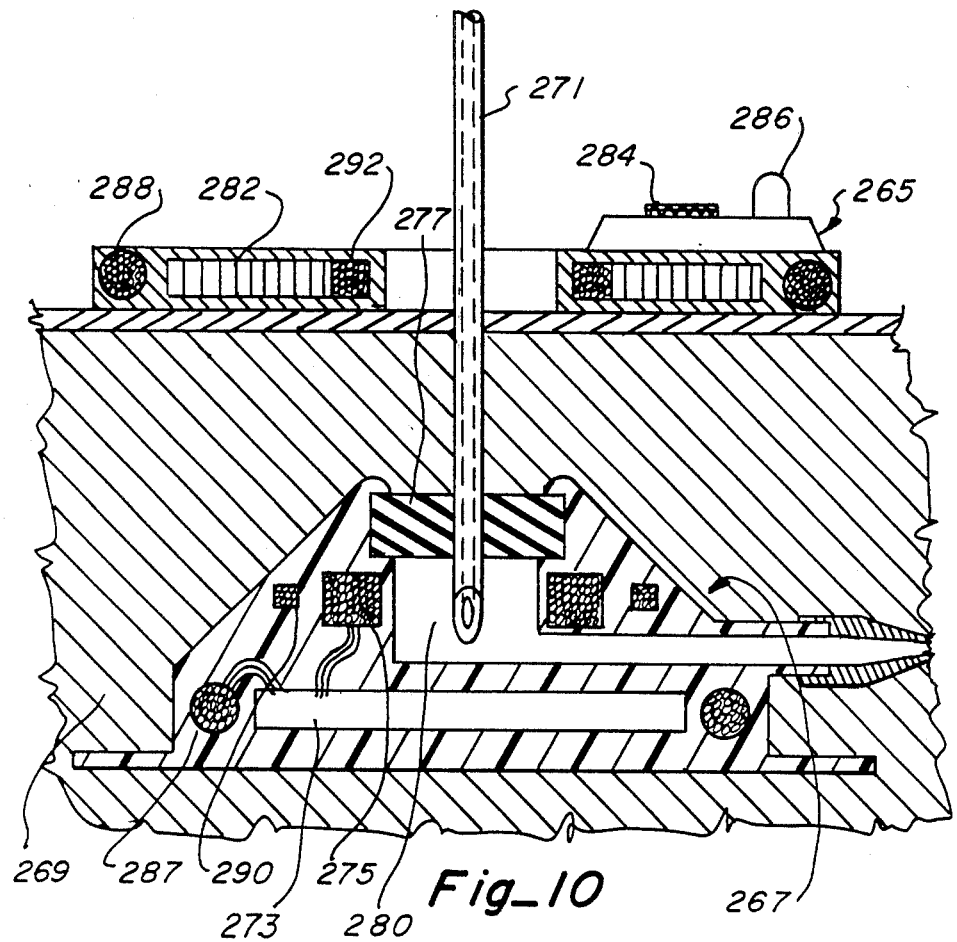
Fig_10
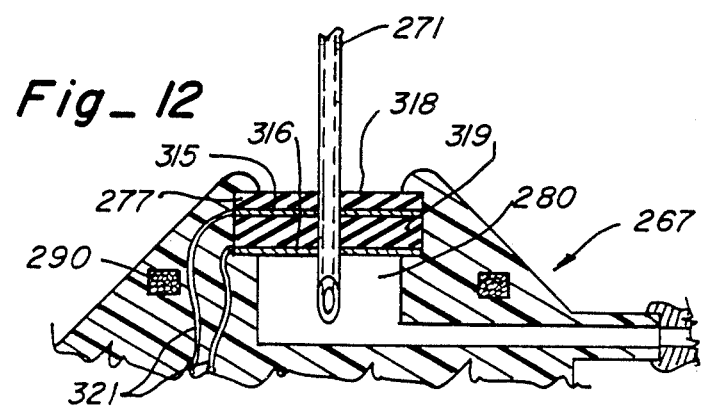
Fig_12

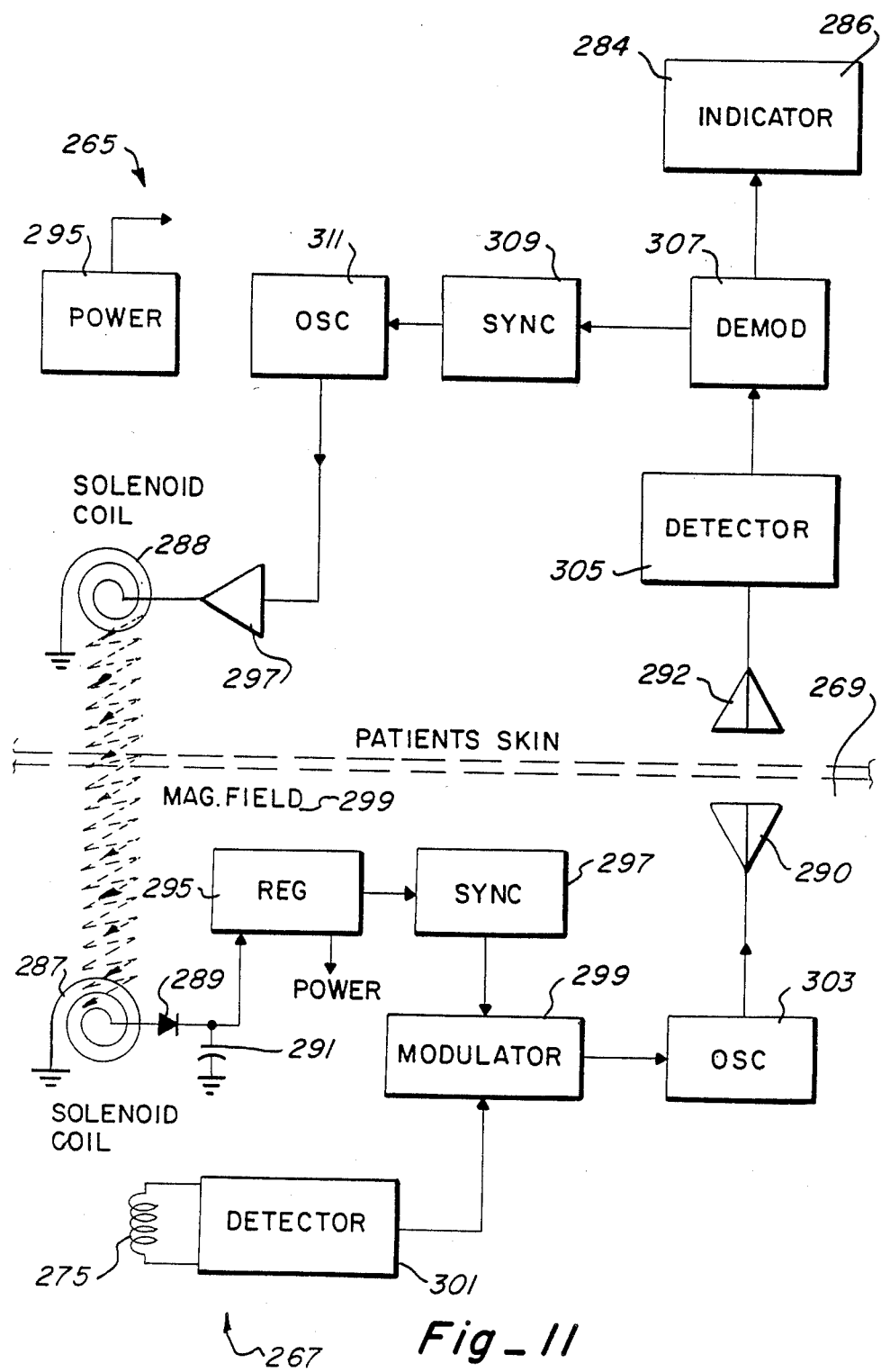
Fig_11

DEVICE AND METHOD FOR PRECISE SUBCUTANEOUS PLACEMENT OF A MEDICAL INSTRUMENT

FIELD OF THE INVENTION

This invention relates to a device and method for the placement of a medical instrument in a body and, more particularly, relates to a device and method for precise placement at a predetermined subcutaneous location of a medical instrumentality insertable into a body and capable of fluid delivery therethrough.

BACKGROUND OF THE INVENTION

Detecting devices for detecting the proximity of metallic objects relative to a selected position are well known and various devices have been heretofore suggested and/or utilized. Examples of such devices can be found in U.S. Pat. Nos. 3,350,660, 3,744,044, 3,889,249, 3,935,542, 4,004,234 and 4,502,042.

Implantable injection cites for receipt or withdrawal of fluids within the human body through a needle are also known and such devices have heretofore been suggested and/or utilized for allowing body cavity access over relatively long terms without unduly limiting the activities and/or movement of a patient (see, for example, U.S. Pat. Nos. 4,160,454 and 4,543,088).

Various sensing devices have also been heretofore suggested and/or utilized in association with stabbing or puncturing medical devices for sensing various parameters of patient penetration by an implement, for example depth of penetration and completion of cavity wall puncture. Examples of such devices are shown in U.S. Pat. Nos. 4,299,230 and 4,535,773.

While such devices now known have been found to be acceptable for some uses, such devices have not been heretofore suggested and/or have not been found to be fully suitable for assuring placement of, and maintenance of, a medical instrument at a desired location to dependably enable a fluid to be inserted into or withdrawn from a predetermined location, and improvements in such devices are deemed to be still useful and/or needed for such application.

SUMMARY OF THE INVENTION

This invention provides a device and method for enabling a user of a fluid delivery medical apparatus insertable into a body to dependably direct the apparatus to a predetermined subcutaneous location for delivery or withdrawal of fluid thereat.

It is an object of this invention to provide a device and method for precise placement of a medical instrument at a predetermined location in a body.

It is another object of this invention to provide a device for directing the placement of a metallic fluid delivery apparatus insertable into a body at a reservoir implanted in the body for fluid delivery thereat.

It is still another object of this invention to provide a device for precise placement of matter at a predetermined location in a body through a medical instrumentality insertable into the body employing a sensor positionable at the predetermined location for sensing the position of the instrumentality relative to the predetermined location, means for signaling the sensed position, and an indicator for receiving the signal and indicating that desired positioning of the instrumentality relative to the predetermined location is established.

It is yet another object of this invention to provide a device for the delivery of medicament to a reservoir implanted in a body through a medical instrumentality insertable into the body having a first sensor positioned contiguous to the reservoir and a second sensor positionable at the surface of the body, wherein the second sensor locates the first sensor relative to a position on the surface of the body suitable for insertion of the instrumentality, and the first sensor locates the instrumentality after insertion relative to the position of the reservoir.

It is still another object of this invention to provide a method of fluid delivery to a predetermined desired location in a body through a medical instrumentality insertable into the body.

It is yet another object of this invention to provide a method for directing insertion of a metallic object into a body for achievement of placement of fluid therethrough at a predetermined location for storage and distribution of the fluid in the body.

With these and other objects in view, which will become apparent to one skilled in the art as the description proceeds, this invention resides in the novel construction, combination and arrangement of parts and method substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a perspective view of a first embodiment of the device of this invention for achieving precise subcutaneous placement of a medical instrument and specifically illustrating the relative positioning of the external and implantable portions of the device when utilized for insertion of a hypodermic needle within the body;

FIG. 2 is a perspective view of the implantable portion of the device shown in FIG. 1;

FIG. 3 is a sectional view taken through section lines 3—3 of FIG. 2;

FIG. 4 is a simplified electronic block diagram illustrating components of the internal portion of the device shown in FIGS. 1 through 3;

FIG. 5 is a simplified electronic block diagram illustrating components of the external portion of the device shown in FIG. 1;

FIG. 6 is a schematic illustration of the electronic circuitry within the implantable portion of the device shown in FIG. 2;

FIG. 7 is a schematic illustration of a portion of the electronic circuitry within the external portion of the device shown in FIG. 1, and particularly illustrating the current monitor and sensing portions thereof;

FIG. 8 is a schematic illustration of a second portion of the electronic circuitry within the external portion of the device shown in FIG. 1, and particularly illustrating the microprocessor, indicators, and optional access ports thereof;

FIG. 9 is a flow diagram illustrating typical operational control of the device shown in FIG. 1;

FIG. 10 is a side sectional view of a second embodiment of the device of this invention for precise subcutaneous placement of a medical instrument;

FIG. 11 is a block diagram illustrating the electronic circuitry of the second embodiment of the device shown in FIG. 10; and FIG. 12 is a partial side elevational view of the implantable portion of a third embodiment of the device of this invention for precise subcutaneous placement of a medical instrument.

DESCRIPTION OF THE INVENTION

A system, or device, 19 for monitoring medical instrument placement within a body to ensure accurate positioning thereof is shown in FIG. 1. System 19 includes an implantable, or internal, portion 21 and an external portion 23 for locating and monitoring internal portion 21 during insertion of an instrument, for example hypodermic needle 25, into human body 27 (while needle 25 is shown it should be understood that system 19 is applicable with other instruments and that the instrument may be of metallic and/or other conductive material).

External portion 23 of system 19 includes hollow collar 30, having instrument access aperture 31 therethrough, and oppositely extending hollow shoulders 32 and 34. External portion 23 provides a housing for electronic circuitry as well as a mounting surface for the external portion 23 of system 19 on the skin of a patient so that the needed indicators and/or, switches utilized are made readily accessible.

As shown, shoulder 32 preferably includes battery access door 36 for access to battery 38 mounted within shoulder 32. Ports 40 may also be provided at shoulder 34 for data communication between the electronic circuitry of system 19 and a computer terminal and/or display. Indicators such as a beeper 42 and an LCD display 44 are provided at shoulder 34 for providing audible and visual indications of the position and status of needle 25 to a user of system 19. Off-on switch 45 is provided in shoulder 34, and push button switch 46 is provided at shoulder 32 for operational mode selection as discussed hereinafter.

Circuitry mounting surfaces, for example, mounting board 48 in shoulder 32 and coil spindle 50 in collar 30, are provided within external portion 23. External portion 23 may be releasably secured to the surface of body 27 in any conventional manner, for example, by adhesive tape 52.

As best shown in FIGS. 2 and 3, implantable portion 21 includes outer enclosure walls 60 which are preferably made of a nonpyrogenic plastic and/or metal material normally impermeable to fluid flow therethrough and substantially insusceptible to erosion due to proximity to body fluids and/or tissue. Septum 62 is provided over passageway 64 extending through throat 66 (which is formed from a nonconductive and nonpyrogenic material) for receipt of needle 25 through septum 62 while remaining substantially impervious to passage through the septum of contaminants from body 27. When implantable portion 21 is properly positioned in a body, septum 62 is facing and substantially parallel to the surface, or skin, of body 27 (as illustrated in FIG. 1).

Outer walls 60 of implantable portion 21 include side wall 68 and base 70. Side wall 60 includes upwardly extending annular shoulder 72 for mounting throat 66 and septum 62. All joints are formed to assure a substantial seal against entry or escape of matter through implantable portion 21 except for delivery or withdrawal of fluid through septum 62 using needle 25 (as illustrated in FIG. 1).

The interior of implantable portion 21 is divided into sealed compartments 75 and 77 by divider wall 79 which may, for example, be an integrally formed portion of side wall 68. Compartment 75, as defined by divider wall 79, is positioned below septum 62 and is a cylindrical reservoir configured to receive and maintain fluid therein (either body fluids for withdrawal from or, for example, medicament for delivery to, the body). Compartment 75 communicates through channel 81 (extending through side wall 68) with body 27, as shown in FIG. 1, and may include catheter 83 at side wall 68 for precise, placement in body 27 of medicament, or the like, metered (by choice of size for channel 81 and catheter 83) from compartment 75.

Compartment 77 houses electronic circuitry for sensing needle position and communicating with external portion 23, as more fully set forth hereinbelow. Compartment 77 may include therein, for example, coil bobbins 85 and 87 attached to base 70, and circuitry compartment 89 between base 70 and divider wall 79 for accommodating circuitry, coils and the like in compartment 77.

FIGS. 4 and 5 are block diagrams illustrating overall operation of the electronic circuitry maintained within implantable and external portions 21 and 23. As shown in FIG. 4, implantable portion 21 includes power input signal receiver 91, voltage regulator 92, oscillator 93 (including coil 94), and modulator 95. As illustrated in FIG. 5, current monitor 97 receives a +V voltage (for example, from battery 38, as indicated in FIG. 1), and external portion 23 also includes power transmitter 99, detector 101, tuned amplifier 103, comparator 105, microprocessor 107, and indicators 108.

As more fully detailed hereinafter, the +V voltage is coupled through current monitor 97 to transmitter 99 for transmission of a power input signal to implantable portion 21 (for example, a magnetic field). The power input signal is received by receiver 91 of implantable portion 21. Shunt voltage regulator 92, coupled with receiver 91, produces a constant voltage for oscillator 93. The frequency of oscillator 93 is capable of being modulated (i.e., varied) by insertion of needle 25 into coil 94. This modulation causes variance of the load at receiver 91 by modulation of regulator 92 through modulator 95. The load variation (in the 100 KHz range) at receiver 91 manifests itself as an amplitude modulation of the magnetic field established in the space between implantable portion 21 and external portion 23 with the magnetic field magnitude decreasing as the load increases.

The indication of loading of receiver 91, coupled to power transmitter 99 of external portion 23, is sensed by detector 101 (for example, an AM diode detector). The signal is amplified and conditioned by amplifier 103 and coupled to comparator 105 for comparison with a reference value, after which the resulting signal is coupled to microprocessor 107 for analysis. Microprocessor 107 provides an input to indicators 108, and responsive to signals received, activates the indicators to thereby guide a user in properly placing needle 25 for fluid delivery therethrough at the desired location.

Turning now to FIGS. 6 through 8, schematic drawings of circuits housed within implantable portion 21 and external portion 23 are provided. Implantable portion 21, as shown in FIG. 6, includes power input signal receiver 91, voltage regulator circuit 92, oscillator circuit 93, and modulator circuit 95. Receiver 91 includes coil 118 to receive and respond to the signal transmitted by coil 120 (shown in FIG. 7) in external portion 23. Coil 118 is wound on bobbin 87 (as illustrated in FIG. 3) and has, for example, a 1.5 inch outside diameter, a 1.25 inch inside diameter and is 0.1 inch across its face. A sufficient number of turns and wire size should be employed to thereby produce, for example, an inductance of 100 uHy. It is, of course, understood that a larger or smaller enclosed area would effect power transfer efficiency and therefor the depth within a body at which coil 118 can be utilized.

Bridge rectifier 122 (having capacitor 123 connected thereacross) receives the signal from coil 118 and produces a D.C. voltage to power the circuitry of implantable portion 21. Voltage regulator 92 includes Schottky diode 126, resistor 128 and transistor 130, and operates as a simple shunt regulator for producing a constant voltage of about one volt to stabilize the frequency of oscillator 93. As shown, rectifier 122 is connected at one side with the anode of Schottky diode 126 and the collector of transistor 130, and is connected at the return side with the cathode of Schottky diode 126 through resistor 128 and with the emitter of transistor 130. The base of transistor 130 is connected to the junction of Schottky diode 126 and resistor 128.

Oscillator 93 includes capacitors 132, 143 and 136, resistors 138 and 140, transistor 142, and coil 94. Coil 94 is wound on bobbin 83 (as illustrated in FIG. 3) and has a 0.1 inch inside diameter and is 0.1 inch long. Using Number 38 wire for 300 turns, an inductance of about 800 uHy may be produced. The collector of transistor 130 is connected through resistor 138 to the base of transistor 142 and through coil 94 to the collector of transistor 142. The base and emitter of transistor 142 are connected with the return lead to rectifier 122 through capacitor 132 and resistor 140, respectively.

Oscillator 114 is free running at about 100 KHz and its frequency is modulated due to insertion of the metallic instrument through coil 94 connected to the collector of transistor 142. The thus modulated frequency, in turn, modulates the loading of coil 118 through modulator 95, which includes resistor 146 (connected with the collector of transistor 142) and transistor 148. Resistor 150 of regulator 92 is connected between bridge rectifier 122 and Schottky diode 126/transistor 130, and is also connected between the emitter and collector of transistor 148, with the emitter also coupled to the return line through capacitor 151 of regulator 92. The loading of coil 118 is thus modulated (i.e., by changes in the oscillator frequency in the implantable portion), which provides a signal that is detectable by detector 101 (through coil 120) in external portion 23 to thereby provide information for determining the positioning status of an instrument inserted through coil 94.

As shown in FIGS. 7 and 8, external portion 23 has a +5 volt source (for example, battery 38 shown in FIG. 1), current monitor 97, power transmitter 99, detector 101, tuned amplifier 103, comparator 105, microprocessor 107, and indicators 108.

The +5 volts is connected through on/off switch 45 to current monitor 97 and power transmitter 99. Transmitter 99 includes transistor 155, the emitter of which is connected with coil 120 to create, for example, a 500 KHz magnetic field to power implantable portion 21. Resistor 157 is connected to the base of transistor 155, and capacitor 150 is connected between the junction of the base of transistor 155 and resistor 157 and one side of coil 120. Capacitors 162 and 163 are connected with the junction of resistor 157 and the collector of transistor 155, and in parallel with coil 120, respectively.

Detector 101 includes diode 165 connected at its cathode to coil 120 and, at its anode, connected through capacitor 167 to the base of transistor 168 of amplifier 103. Diode 165 detects the loading at coil 120 (which is dependent upon the loading of coil 118 of implantable portion 21). Capacitor 169 is connected between the anode of diode 165 and ground, and resister 171 is connected at one side to the junction of diode 165 and capacitors 167 and 169.

Tuned amplifier 103 includes transistor 168, the collector of which is connected with parallel connected coil 177 and capacitor 179. The base of transistor 168 is connected with ground through resistor 181. Transistor 168 operates as an amplifier tuned by coil 177 and capacitor 179 to the frequency of oscillator 93 in implantable portion 21 (for example, being sensitive only to signals in the 100 KHz range, thereby filtering out interfering signals that may otherwise be present in the environment of the device). The output of transistor 168 is coupled from the collector through resistor 183 to one input of operational amplifier 185 of comparator 105.

Pin 3' of operational amplifier 185 is grounded, and pins 2' and 3' have capacitor 189 connected therebetween. Operational amplifier 185 acts as a voltage comparator and provides a square wave output to microprocessor 107 indicative of the frequency of oscillator 93 in implantable portion 21.

In operation, power transmitter 99 acts as an oscillator which, when brought into proper proximity with coil 118 of implantable portion 21, produces a 500 KHz magnetic field for transfer of power to the circuitry of implantable portion 21. Oscillator 93 of implantable portion 21 is a 100 KHz free running oscillator which is detuned by insertion of an instrument into coil 94, for example producing a 99.9 KHz signal upon proper insertion of a needle through coil 94 and a 99.95 KHz signal when the needle is in coil 94 but not properly positioned therethrough. The signal from oscillator 93 causes the load on power input signal receiver 91 to vary dependent upon variation in the oscillator signal by modulation of regulator 92, with the load variation manifesting itself as an amplitude modulation of the magnetic field between coils 118 and 120 (i.e., the greater the load, the smaller the magnetic field).

The amplitude-modulated magnetic field is detected by diode 165 as a voltage signal having the same characteristics as the field. For example, diode 165 detects the signal characteristics indicative of the 99.9 KHz to the 100 KHz load variation and tuned amplifier 103 amplifies the signal. Comparator 105 provides a square wave output signal so that a clean signal, at the same frequency as that of oscillator 93 of implantable portion 21, is made available to microprocessor 107.

Current monitor 97 monitors the overall current of the circuits in external portion 23 by converting the voltage drop across resistor 193 to an oscillator frequency for analysis by microprocessor 107 to indicate if the external portion 23 is properly located on the body over implantable portion 21 thus assuring proper insertion of the instrument through the body and coil 94 of the implanted portion.

Resistor 193 is connected between the base of transistor 195 (as well as the +V voltage supplied to power transmitter 99, detector 101, amplifier 103, and comparator 105) and the +5 volt power supply. The +5 volt power supply is connected through resistor 197 to the emitter of transistor 195. The output of transistor 195 is coupled from the collector to one input (pin 2) of operational amplifier 199 which acts as a voltage comparator having an output frequency which shifts as current changes due to the loading on the circuit caused by the proximity of the circuitry of implantable portion 21 is sensed. Series connected resistor 201 and diode 203 are connected between pins 2' and 6' of operational amplifier 199, capacitor 205 is connected between the collector of transistor 195 and ground, and resistors 207, 209 and 210 are connected with operational amplifier 199 with resistors 207 and 210 providing a voltage divider for supplying a reference voltage to pin 3', and with resistor 209 being connected between pins 3 and 6'.

When the circuitry of external portion 23 is activated by closing on/off switch 45, current monitor 97 monitors the supply current to transistor 155 and tuned amplifier 103. When external portion 23 is brought into physical proximity with implantable portion 21, coils 118 and 120 effectively form a transformer and power is transferred across the 500 KHz magnetic field from external portion 23 to the circuitry of implantable portion 21. The power transfer causes transistor 155 to draw more current from the +5 volt power source with the increased current flow being sensed at transistor 195. A square wave output signal with a frequency proportional to the current drain primarily due to operation of transistor 155 is produced by the current monitor and coupled to microprocessor 107 for measurement. As coils 118 and 120 are brought closer together, the current drain increases until a maximum drain is sensed, for example, a 250 Hz signal representing proper placement of external portion 23 over implantable portion 21, and with 225 Hz and 200 Hz signals representing progressively greater distance from proper placement respectively. Microprocessor 107 receives these signals, and responsive thereto, causes the indicators to display the information contained therein for guiding a user in proper placement of external portion 23 as will be more fully set forth hereinbelow.

Referring now to FIG. 8, microprocessor 107 and indicators 108 are shown in greater detail. Microprocessor 107 is preferably a standard 4 bit CMOS microprocessor (and may be, for example, a MPD7502 manufactured by NEC Electronics) having a 16 bit built-in timer. The microprocessor has latch 211, decoder 212, inverter 213, and AND gates 214 and 215 connected therewith to determine the frequency shifts from current monitor 97 and comparator 105. Latch 211, decoder 212, and AND gates 214 and 215 are connected to RAM unit 216 which serves as the scratchpad memory required by the microprocessor as part of its normal computing capabilities. Inverter 213 and RAM unit 216 are connected with PROM unit 217, having the program in software (which contains the logic necessary for the microprocessor to accomplish its function) burned therein. Clock 218, which includes crystal 219 (having capacitors 220 and 221 at opposite sides thereof), provides the necessary timing signals to microprocessor 107 in a conventional manner.

In this particular microprocessor, the address bus and data bus are multiplexed so that certain pins will output and/or input data as well as output memory addresses. The ALE line on pin 30' indicates when data is available and when addresses are available on the multiplexed pins. Addresses are latched at octal latch 211. Decoder 212 decodes the chip select line (pin 18') of the RAM unit 216.

The software in the microprocessor recalibrates the instrument detection logic periodically (for example, every 30 seconds) to compensate for normal drift of oscillator 93 (on the order of 1%). The recalibration process is simply a taring out of the new oscillator reference frequency at regular intervals.

In general, the chips and design associated with microprocessor 107 herein disclosed implement manufacturers' recommended design for allowing the microprocessor to properly function under the control of BASIC programming located in PROM unit 217.

Indicator circuit 108 includes push button 46 connected between ground and microprocessor 107 for signaling the desired sensing mode to the microprocessor. When push button 46 is depressed, the microprocessor will process the frequency shift information from current monitor 97 to indicator circuit 108 for indication to a user at LED display 44 of proper placement of external portion 23 on body 27 as shown in FIG. 1 (for example, the external portion may be taped to the patient when all three LEDs 44a, 44b and 44c are activated, with progressive activation of first one, then two and finally three LEDs indicating to a user relative nearness to a position suitable for insertion of the instrument). When push button 46 is not depressed, the microprocessor will process frequency shift information from comparator 105 to indicator circuit 108 indicative of the proximity of the instrument to coil 94 of implantable portion 21 and establishment of the instrument therethrough (for example, activation of no LEDs of display 44 indicating either that the needle of FIG. 1 is not near coil 94 or that the device is experiencing malfunction, with activation of "in" LED 44a indicating proper placement of the needle through coil 94, and activation of "out" LED 44c and/or beeper 42 occurring in case of incorrect insertion of the needle and/or disestablishment of the instrument during fluid delivery or withdrawal).

Indicator circuit 108 is connected with voltage source 96 and includes LEDs 44a, 44b and 44c connected to microprocessor 107 and the 5 volt source through resistors 223, 224 and 225, respectively. Hex inverter 227 is connected between microprocessor 107 and LEDs 44 and is also connected to beeper 42 (which is also connected to the +5 volt power source and to microprocessor 107 through capacitor 229).

Also shown in FIG. 8 is optional terminal and/or display ports circuit 231 to facilitate expanded data communication capabilities. Ports 40 include input port 233, output port 234 and port 235 connected to ground.

Input port 233 is connected through resistor 239 to one side of diode 241 and to the base of transistor 243. The emitter of transistor 243 is connected with ground, and the base is connected with ground through diode 241. The collector of transistor 243 is connected to the +5 volt power source through resistor 247 and at pin 10' to microprocessor 107. Resistor 249 is connected between ground and the port 234, which port is connected with collector of transistor 251 through resistor 253. Transistor 251 is connected at its base to pin 11' of microprocessor 107 through resistor 255 and at its emitter to indicator circuit 108.

Microprocessor 107 receives signals from both current monitor 97 and comparator 105, measuring the frequencies of these signals and not their magnitudes. A microprocessor implementation is useful in this device because the relative changes of the two input frequencies are more important than their absolute values. It is much easier for a microprocessor to track moment to moment changes in these two frequencies and make flexible logical decisions about the position of external portion 23 and instrument location with respect to coil 94 than would be the case using a discrete logic device (although such a device could be used).

As will be set forth in more detail hereinbelow, the microprocessor receives an indication that a search for the implant is under way when push button 46 on pin 1' is pressed and held down. The microprocessor logic then looks for increases in the current monitor frequency which is presented to it on pin 14'. If such increases appear, the microprocessor begins to light indicator LEDs 44a, 44b and 44c in response to the amount of increase measured, which is proportional to the amount of coupling between coils 118 and 120 (for example lighting LED 44a when a 200 Hz frequency is presented, LED 44b when a 225 Hz signal is presented, and LED 44c when a 250 Hz signal indicating proper placement of external portion 23 over implantable portion 21 is sensed).

The operator may then remove his finger from button 46 to indicate to the microprocessor that external portion 23 is in position. The microprocessor then remembers that this particular frequency from the current monitor means that the collar is positioned correctly, and can light a warning indicator or other display through port circuit 231 if the current monitor frequency ever varies by more than a set amount from this frequency in the course of later operation thus indicating movement of external portion 23.

The frequency coming into pin 15' from comparator 105 may then be measured and monitored by microprocessor 107 continuously for very small changes which would indicate that a needle has entered the core of coil 94. Changes on the order of 0.1% from the free running frequency (for example 100 KHz) mean that a needle is properly positioned and "in" LED 44a is activated. Changes on the order of 0.05% indicate improper placement of the needle in coil 94 and "out" LED 44c and/or beeper 42 are activated to alert the user. These functions are accomplished by the counting of cycles presented at the microprocessor with 100,000 counts per second corresponding to a lack of proximity of the needle to coil 94 (100 KHz) and with 99,900 counts per second corresponding to proper placement of the needle (99.9 KHz).

The microprocessor can light the LEDs or beep the beeper from pins 2', 3', 4', and 5', which are configured as output ports by the software. The microprocessor can also generate text messages under control of software for transmission to a display (such as a terminal or smart LCD display) by way of its serial ports 231 available on pins 10' and 11'.

The following is a table of illustrative components which may be used to complete much of the circuitry set out in FIGS. 6 through 8. It should be appreciated that while specific component values and/or component production numbers are provided in the table, such values and numbers are for purposes of illustration only and may be modified as required by differing applications.

TABLES OF ILLUSTRATIVE COMPONENTS

| Component | Identifying Number | Value | Component Code # |
|---|---|---|---|
| Implantable Portion | | | |
| Coils | 118 | 100 | |
| (in uHy) | 94 | 800 | |
| Capacitors | 123 | .001 | |
| (in uf unless | 124 | 1 | |
| otherwise | 132 | 470 pf | |
| indicated) | 134 | .0022 | |
|  | 136 | .033 | |
| Resistors | 128 | 47K | |
| (in Ohms) | 138 | 470K | |
|  | 140 | 390 | |
|  | 146 | 47K | |
|  | 150 | 1K | |
| Diodes | 122 |  | 1N4148 |
|  | 126 (Schottky) |  | 1N6263 |
| Transistors | 130, 142, 148 |  | 2N3904 |
| External Portion | | | |
| Coils | 120 |  | (2" diameter; 5 turns #26 wire) |
| (in uHy unless otherwise indicated | 177 | 1 mHy | |
| Capacitors | 162 | 33 @ 4 v | |
| (in uf unless | 159 | .0022 | |
| otherwise | 163 | .0047 to .033 | |
| indicated) | 167 | .0022 | |
|  | 169 | .0022 | |
|  | 179 | .0022 | |
|  | 189 | 100 pf | |
|  | 205 | .0022 | |
|  | 229 | 10 | |
| Resistors | 157 | 10K | |
| (Ohms) | 171 | 27K | |
|  | 181 | 1 M | |
|  | 183 | 10K | |
|  | 193 | 47 | |
|  | 197 | 1 M | |
|  | 201 | 47 | |
|  | 207 | 4.7 M | |
|  | 209 | 4.7 M | |
|  | 210 | 4.7 M | |
|  | 223, 224, 225 | 510 | |
|  | 239, 247 | 4.7K | |
|  | 249 | 470 | |
|  | 255 | 1K | |
|  | 253 | 47 | |
| Diodes | 165, 203 |  | 1N4148 |
|  | 219, 220, 221 | (LED) | |
| Transistors | 155 |  | 2N2222 |
|  | 168, 195 |  | 2N3906 |
| Operational Amplifiers | 185 |  | TLC271 |
|  | 199 |  | 7611 |
| Microprocessor | 107 |  | 8052 |
| Latch | 211 |  | 74HC373 |
| Decoder | 212 |  | 74HC138 |
| Inverter | 213 |  | 74LS05 |
| AND Gates | 214, 215 |  | 74HC08 |
| RAM | 216 |  | 8416 |
| PROM | 217 |  | 2732 |

Turning now to FIG. 9, a flowchart illustrating typical operational control by the software of system 19 for monitoring instrument placement is set forth. After applying power to the system, housekeeping details are initially undertaken (initialization, battery check, and the like). The system then scans to see if push button 46 is depressed, and if so, the frequency of the current monitor is read and the LED display is driven responsive to the frequency information from current monitor 97.

At such time as the implantable portion is located and the push button is no longer depressed, the LEDs will be cleared, and the system will proceed to read the frequency from comparator 185. The system first checks to determine whether the system is operational (i.e., if any reportable frequency is being received), and, if not, may cause a message to be printed at an auxiliary device at data ports 231. Once a determination is made that the system is operational, reading of the frequency continues to determine needle status in coil 94. If a large deviation from proper position is sensed, the system checks for the possibility of any required drift correction (of oscillator 93), and if required the system resets to the current comparator frequency and continues to check for needle status.

Thereafter, the operational routine is reinstituted, and, if the system is found to be operational, the system will again inquire as to the status of the instrument through coil 94 (as shown in FIG. 6). Once the needle is properly established, the "in" LED is activated and a message is printed at auxiliary devices, if any, to indicate the establishment of the instrument through the coil. Recalibration of the needle oscillator frequency, if required, continues, for example, every 30 seconds. If the needle is in but not correctly positioned in coil 94, or if the needle becomes dislodged, the "out" LED and/or beeper are activated accordingly (and a message is printed at the auxiliary device, if any).

Thereafter, the system will proceed to determine if the needle has been removed if a large deviation from proper positioning is sensed. If the needle has been removed, the LEDs are deactivated (and a message is printed at any auxiliary unit in place), the beeper is activated, and the routine is reset for continued reading of the frequency from comparator 185.

Turning back to FIGS. 1 through 3, use of the device may be illustrated. Implantable portion 21 is surgically positioned in the body of a patient for delivery of fluid through catheter 83. External portion 23 is activated by the user with on/off switch 45. Mode selection switch 46 is then depressed and a user manually manipulates external portion 23 along the body 27 of a patient until LED 44a is activated indicating activation of internal portion 21 and nearness to proper positioning of external portion 23 over internal portion 21. Further manipulation by the user in a proper direction on the body of the patient will cause activation of LED 44b indicating even closer proximity and, ultimately, LED 44c indicating placement at a position suitable for insertion of needle 25 into the body 27 of the patient for placement of the needle through septum 62 of internal portion 21.

The user may then release mode selection switch 46 and tape external portion 23 at shoulders 32 and 34 to the body of the patient. Microprocessor 107 (shown in FIG. 5) stores the particular frequency then reads from current monitor 97 corresponding to correct positioning of external portion 23. Optionally, microprocessor 107 could cause activation of a warning indicator if the current monitor frequency varies by more than a set amount in the course of later operations indicating displacement of the external portion.

Needle 25 may then be inserted into the patient's body through access aperture 31 and moved toward implanted portion 21. As needle 25 approaches passageway 64 through throat 66 of implanted portion 21, the effect of the metallic needle's proximity to coil 94 will cause "out" LED 44c to be activated indicating nearness to proper placement of the open end of the needle to fluid comparment 75. When needle 25 is properly positioned through coil 94 and in compartment 75, "in" LED 44a will be activated indicating achievement of proper placement.

The user may, while "in" LED 44a is activated, deposit fluid (medicament for example) through needle 25 into compartment 75 for storage thereat and ultimate delivery thereof through catheter 83 to the body of the patient. If, at any time during fluid deposit, needle 25 should become dislodged or otherwise undesirably positioned, the user will be alerted by deactivation of LED 44a and activation of beeper 42 and "out" LED 44c.

Alternative embodiments of the invention are shown in FIGS. 10 through 12. While two alternative embodiments are shown therein, their inclusion in this description is not meant to indicate that all possible alternative embodiments are exhausted by such showing. Multiple methods of detecting needle penetration and position, as well as implant position, have been investigated, including but not necessarily limited to, location by sensing change in capacitance, resistance, and/or impedance, as well as the use of a current injection through the instrument and received by the implant and sensing of such current in the implant by the external portion of the device.

FIGS. 10 and 11 show an embodiment of the invention in many ways similar to the embodiment heretofore shown, and includes external portion 265, internal portion 267, with internal portion 267 being implanted in body 269 and in receipt of needle 271. The primary distinction between the embodiment shown in FIGS. 10 and 11 and the embodiment heretofore described is the use of telemetry circuit 273 connected to sensor coil 275 such that when needle 271, or some other accessory, fully penetrates septum 277 and is in proper working position, sensor 275 will change its transduction characteristics sufficiently to be detectable by telemetry circuit 273. As shown herein, coil 275 may be an air inductor or a cored inductor employed in an eddy current detection circuit.

In the case of an air inductor, invasion of the core axially by a conductive material will alter the inductor's impedance. In the case of the eddy current detector, proximity of a magnetic material to the core changes the impedance of the inductor. Such impedance changes are relatively easily detected. It is, of course, apparent that, optionally, the sensor may be optical or a switch closer as more fully set forth here with regard to FIG. 12. However, the avoidance of moving parts is highly desirable, thus rendering the field disturbance detectors the better choice.

The detector circuitry applies an appropriate signal to the telemetry transmitter circuitry such that the telemetered transmission contains information as to the presence or absence of the penetrating accessory within antechamber 280. The telemetered transmission is received by receiver circuitry 282 in external portion 265. As long as needle 271 remains in the working zone of antechamber 280, the receiver's audible alarm 284 remains silent, and visual indicator 286 clearly indicates proper placement.

At any time the needle fails to stimulate the sensor, time not being in the working position, the receiver activates audible alarm 284 and changes the state of visual indicator 286.

The telemetry device contains no power source of its own, but is magnetically coupled by coil 287 to the external power source, coil 288. Transmission from the implanted transmitter through antenna 290 is received by antenna 292 in external portion 265. Transmission from the implanted transmitter is not continuous, but occurs only when the external device first radiates a burst of energy, which is rectified and stored in a capacitor in implanted portion 267. The energy burst also serves as a signal to start transmission from the implant. The transmission consists of a burst of radiated energy, preferably a radio frequency, at a frequency clearly distinguishable from that of the energizing field. The receiver then detects the synchronous transmission burst and demodulates the signal to determine whether the instrument is properly placed within the antechamber, thereby activating the appropriate indicators.

As shown in FIG. 11, power source 295 provides the power necessary to activate coil 288 through coil driver 297. Magnetic field 299 is thereby generated and received by internal coil 287 coupled with diode 289, an AC to DC converter, and through capacitor 291 to ground.

Regulator 295 receives power from coil 287 and is connected to synchronizer 297, for synchronous modulation of signals, and to modulator 299. Field detector coil 275 is connected through detector circuitry 301 and to modulator 299, thereby modulating the power signal which modulated signal is then directed through oscillator 303 to antenna 290. The signal from antenna 290 is received by antenna 292 in external portion 265 connected to detector circuitry 305. The detected signal is then demodulated by demodulator 307 connected to synchronizer 309 for synchronizing the power circuit, and to oscillator 311 for producing a more readily identifiable, noise-free information channel. The signal from the implant may be processed directly to indicators 284 and 286.

As is true with all embodiments of the device of this invention, the receiver may optionally be linked electronically to a drug delivery device to directly enable or disable drug flow, depending upon the detected state of the instrument within the implant.

Turning to FIG. 12, a third embodiment of the device is shown being similar in many ways to the device shown in FIG. 10, and which could be employed in devices using either telemetered transmission or the techniques discussed with respect to FIGS. 6 and 7. Internal portion 267 is again illustrated with needle 271 properly positioned in antechamber 280 for delivery of fluid thereto or withdrawal of fluid therefrom. The primary distinction is the utilization in this embodiment of conductive rubber strips or layers 315 and 316 placed between insulating silicone layers 318 and 319 in septum 277. The conductive rubber layers are connected by wires 321 to, for example, the telemetry circuit 273 of FIG. 10. When the needle is properly positioned through the septum and in contact with the conductive rubber layers 315 and 316, the two otherwise insulated conductive layers are shorted thereby closing a circuit and activating the telemetry circuit.

As may be appreciated from the foregoing, a device and method for the precise subcutaneous placement of a medical instrument, for example a hypodermic needle, for delivery of fluid to a precise subcutaneous location, or withdrawal of fluid therefrom, is shown and wherein an external portion placable on the surface of the body includes circuitry for locating an implantable portion placed at the subcutaneous location, and with the internal portion including circuitry for sensing the proximity of the instrument to the desired location and establishment of the instrument thereat and for signaling such proximity and establishment of the instrument to a user of the device.

What is claimed is:

1. A system for monitoring medical instrument placement with respect to a reservoir in a body to ensure accurate positioning of an opening in an inserted end portion of said instrument at a preselected location with respect to reservoir, said system comprising:
   electrical means positioned outside said body for providing an electrical power output;
   signal generating means positioned outside said body connected with said electrical means for receiving said electrical power output to thereby supply output signals;
   sensing means separate from connection with said instrument and adapted to receive said output signals from said signal generating means, said output signals being modified in accordance with the position of said instrument with respect to said reservoir, to thus utilize said signals to provide an electrical output indicative of at least a predetermined desired positioning of said inserted end portion of said instrument at said preselected location within said body;
   signaling means connected with said sensing means to receive said electrical output therefrom and responsive thereto provide an electrically induced output signal; and
   indicating means receiving said output signal from said signaling means and utilizing said output signal to provide an indication at least that said desired positioning of said inserted end portion of said instrument at said preselected location is then established.

2. The system of claim 1 wherein said inserted end portion of said instrument includes a metallic material, and wherein said sensing means includes an electrically inductive coil said output indicative of a predetermined desired position of said inserted end portion of said instrument being provided upon insertion of said end portion to attain a predetermined position with respect to said coil.

3. The system of claim 2 wherein said sensing means includes an oscillator and said coil is included in said oscillator, and wherein said signaling means includes signal modulation means for varying said output signal in response to said output from said sensing means.

4. The system of claim 1 wherein said indicating means includes microprocessor means for processing said electrically induced output signal from said signaling means.

5. The system of claim 1 wherein said instrument effects fluid delivery therethrough, wherein said body has reservoir means placed therein at said preselected location for one of receipt of said fluid through said opening in said inserted end portion of said instrument and maintaining said fluid therein for withdrawal of said fluid through said opening in said inserted end portion of said instrument, and wherein said reservoir means includes fluid passageway means for passage of said fluid between said reservoir means and said body.

6. The system of claim 1 wherein said inserted end portion of said instrument is made of electrically conductive material and wherein said sensing means includes first and second electrically conductive means, said sensing means providing said output indicative of said predetermined desired position of said inserted end portion of said instrument when said inserted end portion is in electrical contact with both said first and second conductive means.

7. The system of claim 1 wherein said sensing means provides outputs indicative of proximity of said inserted end portion of said instrument to said preselected location within said body.

8. A system for locating matter at a predetermined position within a body, which position is accessible through a medical instrumentality insertable into said body, said system comprising:
reservoir means positioned at said predetermined position within said body for receiving and maintaining said matter thereat;
first electronic means contiguous to said reservoir, said first electronic means including sensing means separate from connection with said medical instrumentality for sensing the position of said instrumentality relative to said reservoir means and signaling means connected with said sensing means for providing an electrical signal indicative at least of positioning of said instrumentality within said reservoir means;
second electronic means positioned outside said body, said second electronic means including signal processing means for sensing said electrical signal provided by said signaling means and indicating means for indicating to a user of said instrumentality said positioning of said instrumentality within said reservoir means responsive to said electrical signal sensed by said signal processing means; and
electrical signal generating means positioned outside said body for activating said first and second electronic means of said system.

9. The system of claim 8 wherein said signaling means includes means for providing a signal indicative of the proximity of said instrumentality to said reservoir means and wherein said indicating means of said second electronic means includes means for indicating to a user of said instrumentality said proximity of said instrumentality to said reservoir means.

10. The device of claim 8 wherein said sensing means is a proximity detector for sensing the positioning of said instrumentality relative to said reservoir means.

11. The device of claim 8 wherein said reservoir means includes a first section for receiving said instrumentality therethrough while remaining substantially impervious to passage of matter from said body therethrough, and a second section for storing said matter received through said instrumentality, said second section being adapted for metered delivery of said matter from said second section to said body.

12. A device for locating and establishing placement relative to a desired location in a body of a medical instrumentality insertable into said body for effecting fluid delivery to said desired location, said device comprising:
first means implanted within said body and contiguous to said desired location, said first means including first electronic sensing means for sensing inductance changes caused by positioning of said instrumentality inserted into said body relative to said desired location and signaling means for providing an electrically induced signal indicative of said inductance changes; and
second means movably positionable outside said body, said second means including second electronic sensing means for sensing the position of said first means relative to a location on said body suitable for insertion of said instrumentality and providing an electrical signal indicative thereof, signal receiving and processing means for receiving and processing said signals from said second electronic sensing means and said signaling means, and indicating means connected with said signal receiving and processing means for indicating to a user of said instrumentality when said instrumentality is suitably positioned for insertion and when said instrumentality is positioned at said desired location.

13. The device of claim 12 wherein said first and second means include cooperative electrical energizing means for energization of said first electronic sensing means, said signaling means, said second electronic sensing means, said signal receiving and processing means and said indicating means.

14. The device of claim 13 wherein said second electronic sensing means includes monitoring means for monitoring said cooperative energizing means, and wherein said location on said body suitable for insertion of said intrumentality is indicated by said indicating means when maximum energization of said first sensing means and said signaling means is sensed by said second sensing means.

15. The devide of claim 13 wherein said electrical signal indicative of said inductance changes is one of a radio signal and a signal indicative of a relative change of said energization corresponding to said positioning of said instrumentality with maximum relative change of said energization corresponding to placement of said instrumentality at said desired location.

16. The device of claim 15 wherein said first electronic sensing means includes induction means and oscillator means, and wherein said inductance changes are caused by positioning of said instrumentality relative to said induction means.

17. The device of claim 12 wherein said second means further includes microprocessor means connected to said receiving and processing means, and said indicating means.

18. A circulatory system accessing device for enabling repeated, precise placement of fluid in a body at a predetermined location through a metallic object capable of fluid delivery therethrough, said device comprising:
an implantable portion positionable in said body at said predetermined location;
an external portion positionable on the surface of said body including transmitting means for transmitting an electrically induced input signal;
chamber means in said implantable portion having a first section for receiving said metallic object therethrough while remaining substantially impervious to passage of matter from said body therethrough, a second section for storing said fluid delivered through said metallic object, and a passageway for delivery of said fluid from said second section to said circulatory system;
sensing means in said implantable portion adjacent said first section of said chamber means for sensing the position of said metallic object relative to said first section of said chamber means and establishment of said metallic object through said first section of said chamber means;
signaling means connected with said sensing means in said implantable portion for providing a signal indicative of said sensed relative position and said establishment of said metallic object through said first section of said chamber means;

input signal receiving means connected with said sensing means and said signaling means in said implantable portion for receiving said electrically induced input signal from said transmitting means of said external portion thereby activating and making operational said sensing means and said signal generating means of said implantable portion;

sensing means in said external portion for locating said implantable portion relative to a position on the surface of said body suitable for insertion of said metallic object and producing a signal indicative thereof;

signal receiving means in said external portion for receiving said signal indicative of said sensed relative position and achievement of placement of said metallic object from said signaling means of said implantable portion;

processing means connected with said sensing means and signal receiving means of said external portion and including indicator means for indicating to a user of said metallic object said position suitable for insertion, said sensed relative position of said metallic object to said first section of said chamber means and establishment of said metallic object through said first section of said chamber means; and battery means connected with said transmitting means, said sensing means, said signal receiving means and said processing means of said external portion.

19. The device of claim 18 wherein said transmitting means of said external portion includes driver means with coil means connected thereto for generating a magnetic field.

20. The device of claim 19 wherein said input signal receiving means of said implantable portion includes coil means, rectifier means and capacitor means for receiving said operational input signal and producing a voltage for said sensing means, and regulator means to cause said voltage to remain constant.

21. The device of claim 20 wherein said sensing means of said implantable portion includes oscillator means connected to said regulator means and coil means connected to said oscillator means and adjacent said first section of said chamber means and configured for receipt of said metallic object therethrough whereby the frequency of said oscillator means is modulated by the relative position of said metallic object to said coil means.

22. The device of claim 21 wherein said signaling means of said implantable portion includes modulation means connected to said oscillator means and said power input signal receiving means whereby said frequency of said oscillator means modulates said signal received by said coil means of said power input signal receiving means.

23. The device of claim 22 wherein said signal receiving means of said external portion includes detection means for detecting said modulated loading of said coil means of said power input signal receiving means and producing a signal indicative thereof, amplifier means connected to said detection means for amplifying said signal indicative thereof, and comparator means connected with said amplifier means and said transmitting means of said external portion for providing an output to said processing means indicative of said modulated frequency from said sensing means of said implantable portion.

24. The device of claim 23 wherein said sensing means of said external portion includes current monitoring means connected to said battery means, said transmitting means and said signal receiving means of said external portion whereby the overall current of said external portion is monitored and an output indicative of said overall current is provided to said processing means.

25. The device of claim 18 wherein said indicator means of said processing means provides at least one of a visual indication of said sensed relative position of said metallic object to said first section of said chamber means and positioning of said metallic object through said first section of said chamber means and an audible indication of disestablishment of said metallic object through said first section of said chamber means subsequent to said establishment thereof.

26. The device of claim 18 where said first section of said chamber means is a septum and wherein said third section of said chamber means is a catheter.

27. A method of monitoring placement of a medical instrument within a body to insure accurate positioning of an opening in the inserted end portion of said instrument relative to a predetermined desired location in said body comprising:

utilizing an electrical power output to generate a first signal from a first position outside said body;

inserting said end portion of said instrument into said body at a position on the surface of said body adjacent said predetermined desired location in said body;

moving said inserted end portion of said instrument toward said predetermined desired location;

receiving said first signal at a second position separate from connection with said instrument and utilizing said first signal to sense when said inserted end portion arrives at said predetermined desired location;

providing an electrical output indicative at least of positioning of said opening in said inserted end portion of said instrument at said predetermined desired location;

utilizing said electrical output indicative at least of positioning to provide an electrically induced output signal; and utilizing said electrically induced output signal to indicate to a user establishment of said desired placement of said opening in said inserted end portion of said instrument at said predetermined desired location.

28. The method of claim 27 including the step of sensing the relative proximity of said inserted end portion of said instrument to said predetermined desired location while said inserted end portion is being moved toward said predetermined desired location and indicating said relative proximity to said user.

29. A method for directing insertion of a metallic object having an open end portion into a body for achievment of desired placement of a fluid therethrough at a predetermined location in said body comprising:

positioning a reservoir at said predetermined location in said body;

providing an electrical power output outside of said body;

utilizing said electrical power output to generate a first signal from a position outside said body;

utilizing said first signal to sense the location of said reservoir relative to a position on the surface of said body suitable for insertion of said metallic object and indicating said position suitable for insertion to a user of said metallic object;

inserting said open end portion of said metallic object into said body at said suitable position;

moving said open end portion of said metallic object toward said reservoir;

receiving said first signal at a position inside said body and utilizing said first signal to sense movement of said open end portion of said metallic object into said reservoir;

providing an electrical output indicative at least of movement of said open end portion of said metallic object into said reservoir;

utilizing said electrical output indicative at least of movement to provide an electrically induced output signal;

utilizing said electrically induced output signal to indicate to a user establishment of the desired placement of said open end portion of said metallic object within said reservoir; and effecting fluid delivery through said metallic object to said reservoir while said desired placement of said open end of said metallic object within said reservoir is maintained.

30. The method of claim 29 including the step of sensing the proximity of said inserted open end portion to said reservoir while said inserted open end portion is being moved toward said reservoir and indicating said proximity to said user.

* * * * *

UNITED STATES PATENT AND TRADEMARK OFFICE
CERTIFICATE OF CORRECTION

PATENT NO. : 4,804,054

DATED : February 14, 1989

INVENTOR(S) : Howson et al.

It is certified that error appears in the above-identified patent and that said Letters Patent is hereby corrected as shown below:

Column 3, line 4, "elevational" should be --sectional--.

Column 5, line 25, "143" should be --134--.

Column 5, line 66, "150" should be --159--.

Column 7, line 2, "2" should be --2'--.

Column 7, line 14, "3" should be --3'--.

Column 12, line 19, "injection" should be --injected--.

Column 12, line 60, "time" should be --thus--.

Column 14, line 6, "reservoir" should be --said reservoir--.

Column 14, line 36, "coil" should be --coil,--.

Column 16, line 25, "devide" should be --device--.

Signed and Sealed this

Twenty-second Day of August, 1989

Attest:

DONALD J. QUIGG

Attesting Officer

Commissioner of Patents and Trademarks